United States Patent [19]
Tully

[11] Patent Number: 6,127,425
[45] Date of Patent: *Oct. 3, 2000

[54] ORAL LIQUID MEDICINE SOLUTION

[75] Inventor: Roger Edward Tully, Ilkley, United Kingdom

[73] Assignee: Akzo Nobel N.V., Arnhem, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 09/106,172

[22] Filed: Jun. 26, 1998

[30] Foreign Application Priority Data

Jun. 27, 1997 [EP] European Pat. Off. .............. 97201964

[51] Int. Cl.$^7$ ......................... A01N 33/02; A61K 31/135
[52] U.S. Cl. ........................... 514/648; 514/651; 568/328
[58] Field of Search .................................. 514/648, 651; 564/324

[56] References Cited

U.S. PATENT DOCUMENTS 4,851,433  7/1989  Kraus ....................................... 514/648

FOREIGN PATENT DOCUMENTS

| 240131 | 10/1987 | European Pat. Off. . |
|---|---|---|
| 293263 | 8/1991 | Germany . |
| WO 8401506 | 4/1984 | WIPO . |
| WO 9311757 | 6/1993 | WIPO . |
| WO 9416733 | 8/1994 | WIPO . |
| WO 9511013 | 4/1995 | WIPO . |
| WO 9700669 | 1/1997 | WIPO . |
| WO 9706782 | 2/1997 | WIPO . |

*Primary Examiner*—Frederick Krass
*Attorney, Agent, or Firm*—Mary E. Gormley

[57] ABSTRACT

Found is a pharmaceutical preparation which provides Tamoxifen Citrate in a liquid dosage form, viz. as an oral solution. The finding is based on a solvent comprising the following components: (a) of from 10% to 20% by weight of ethanol, (b) of from 10% to 60% by weight of a glycol; and (c) water, optionally containing additives, in a volume percentage adding up to 100% by volume. A preferred additive is sorbitol.

11 Claims, No Drawings

ORAL LIQUID MEDICINE SOLUTION

FIELD OF THE INVENTION

The invention is in the field of pharmaceutical compositions comprising, as a medicinally active ingredient, Tamoxifen. Tamoxifen is known as a medicine for the treatment of breast cancer and anovulatory infertility.

BACKGROUND OF THE INVENTION

Pharmaceutical preparations which provide a dosage form of Tamoxifen are known the dosage form being solid, viz. tablets having strengths of the medicinally active ingredient of from 10 mg Tamoxifen. The Tamoxifen regularly is present in the form of the corresponding citrate, ethanamine, 2-4-(1,2-diphenyl-1-butenyl)phenoxy)-N,N-dimethyl-(Z)-, 2-hydroxy-1,2,3-propanetricarboxylate (1:1), the IUPAC name of which is (Z)-2-[4-(1,2)-Diohenylbut-1-enyl) phenoxy]ethyldimethylamine citrate.

Although the known tablets are generally acceptable as far as their medicinal activity is concerned, the solid dosage form imposes restrictions on the pharmaceutical use of Tamoxifen. Some patient populations have a difficulty, physical or psychological, in swallowing solid dosage forms. If a liquid dosage form were available, these patients could more easily take the required dose of Tamoxifen, having it administered in the form of an oral liquid preparation or, e.g., by means of a naso-gastric tube.

However, such oral liquid preparations of Tamoxifen are neither available on the market, nor even known in the art. To manufacture a liquid preparation of Tamoxifen presents a problem to the person skilled in the art, as the compound has a poor solubility in pharmaceutically acceptable solvents and in view of the general difficulty in predicting the solubility of specific pharmaceutical salts such as Tamoxifen Citrate in any given liquid.

SUMMARY OF THE INVENTION

Hence, it is an object of the present invention to provide a liquid capable of dissolving Tamoxifen Citrate in a sufficiently high concentration. It is particularly desired to provide a solution of Tamoxifen Citrate in which the concentration of Tamoxifen is high enough to correspond to the concentration of the regular Tamoxifen tablets. A further object of the invention, is to find a method of dissolving Tamoxifen Citrate without chemically altering it, i.e., the use of known, solubility-enhancing, complexing agents is not preferred according to the invention.

Without detracting from the theoretical possibility that the Tamoxifen is present in another form, it will as a rule be the above-identified citrate. A further problem that may be incurred with this compound, is that its crystals exist in two polymorphic forms. The normally available compound is present as the meta stable polymorph. On crystallisation from protic solvents, the compound forms crystals of the stable polymorph. The stable polymorph exhibits undesirable characteristics, int.al., even further reduced solubility. These undesirable characteristics may affect the absorption behaviour in vivo, thereby reducing the bioavailability of the compound. The presence of these polymorphic forms precludes the formulation of Tamoxifen Citrate as a suspension. For, even with the low intrinsic solubility of the molecule, a small amount would enter (aqueous) solution and then leave it, crystallising in the less desirable polymorphic form. Hence, it is a further object of the invention to provide a liquid formulation of Tamoxifen Citrate where crystallisation will not occur.

DETAILED DESCRIPTION OF THE INVENTION

The invention provides a liquid mixture satisfying the above demands. Thus according to the present invention Tamoxifen is provided in a novel dosage form, viz. as a solution of at least approximately 1.5 mg/ml, and preferably of from 3 to approximately 6 mg/ml.

The possibility of providing Tamoxifen in the form of an oral solution can be considered a new and surprising achievement per se. It is particularly the determination of a suitable solvent combination which overcomes the technical problem of providing a Tamoxifen Citrate solution of sufficiently high concentration. The solvent system in accordance with the invention comprises the following components:

(a) from 10% to 20% by weight of ethanol,
(b) from 10% to 60% by weight of glycol; and
(c) water in a volume percentage adding up to 100% by volume.

Incidentally, in DD 293 263 it has been disclosed to mix tamoxifen with a minor amount of ethanol and polyethylene glycol, but this does not yield a solution.

The ethanol component (a) preferably is employed in about 15% by weight. If less than about 10% is used, the desired physical stability of the solution may be jeopardised, e.g. undesired crystallisation may occur upon storage at low (2–8° C.) temperatures. The upper limit is mainly determined by practical reasons. Too high a percentage of ethanol is undesirable in view of the flammability hazards during processing and the potential for evaporative losses during manufacture. Ethanol has a very discernible effect on taste perceptions when present at concentrations in excess of 20%. Hence, it is generally desired to keep ethanol concentrations as low as possible. The present invention allows using a relatively loss concentration of ethanol.

For the sake of obtaining a chemically stable formulation, the glycol component (b) may, in principle, consist of any (poly) glycol, e.g. polyethylene glycol of varying molecular weights, but for the desired organoleptic characteristics, i.e. mouthfeel and flavour, it is preferred for the glycol to be a low molecular weight glycol or glycerol. The low molecular weight glycol preferably is propylene glycol, glycerol, or a mixture thereof. If propylene glycol is employed, the preferred percentage thereof is about 10% by weight. If the percentage is decreased, care should be taken to maintain a physically stable solution. Due to the burning taste displayed by propylene glycol, too high a percentage thereof should preferably be avoided. If glycerol is employed, the percentage thereof preferably is about 40% to 50% by weight. The percentage may be increased, but care should be taken that the resulting formulation does not become too viscous for processing. The percentage may also be decreased, but in view of the relative increase of the amount of water, care should be taken that the Tamoxifen Citrate still dissolves to a sufficient extent. It is preferred for the glycol component (b) to consist of a mixture of about 10% by weight of propylene glycol and of from about 40% to 50% by weight of glycerol.

The water component (c) may comprise any suitable, conventional additive, such as flavours, sweeteners, and colouring agents. Particularly preferred additives are bulk-sweetening agents such as sucrose, or any other sugar, hydrogenated glucose, or any other modified sugar, or—most preferably—sorbitol. The sugars may be added as dry powders or, preferably, as solutions. The preferred sorbitol solution is a non-crystallising solution containing 70% by weight of sorbitol. In all cases care should be taken that the resulting aqueous solution is still processable. In this respect, sorbitol preferably is employed in an aqueous solution of from 15% to 25% by weight, and most preferably about 20% by weight.

Within the teaching of the present invention, the person of ordinary skill in the art is capable, of taking the required care to provide, without undue experimentation, a solution on the basis of the above components (a) through (c) which, on the one hand has sufficient stability and, on the other hand does not have such a high viscosity as to become unworkable.

In terms of a solution which is the most stable, allows the dissolution of a relatively high percentage of Tamoxifen Citrate, and which maintains ease of processing, the most preferred formulation is a solvent mixture comprising 15% by weight of ethanol, 10% by weight of propylene glycol, 50% by weight of glycerol, and 20% by weight of a sorbitol solution, the remainder being water to the required volume. The formulation according to the invention provides a physically and chemically stable solution of Tamoxifen Citrate at the requited concentration.

The solution of the invention can be prepared by first making a mixture of the ethanol and glycol components, and then adding, generally under stirring, the required quantity of Tamoxifen Citrate. After complete dissolution, if present the optional ingredients, such as sorbitol and flavours, and water are added. According to the invention another method was found to be the following. First, Tamoxifen Citrate, in the desired quantity, is pre-dispersed in the glycol component, and then ethanol is added to complete dissolution. After dissolution, the remaining components are added, as explained above. This method is highly efficient, and therefore preferred, in the case of a glycol component that consists of a mixture of propylene glycol and glycerol. In that case, the Tamoxifen Citrate is first dispersed in the propylene glycol, using any conventional dispersion technique but, preferably, high shear mixing. The dispersion is added to the glycerol and, on addition, of the ethanol component, generally under stirring, a complete solution is rapidly achieved.

The invention will be further explained hereinafter with reference to the Examples.

EXAMPLES I

A quantity of 3.04 g of micronised Tamoxifen Citrate is dispersed, using high shear mixing, in 100.00 g of propylene glycol. The resulting dispersion is added to 450.00 g of glycerol and mixed to produce a homogeneous suspension. Then 150.00 g of ethanol is added and the mixture is stirred until a clear, bright, colourless solution is obtained. Subsequently, 200.00 g of a 70% by weight solution of sorbitol is added, as well as 2.00 g of flavours. Upon stirring, sufficient water is added to make to a volume of 1000 ml. Thus, a stable formulation of dissolved Tamoxifen Citrate is obtained.

EXAMPLE OF COMPARISON

In this Example, a comparison is made of several solvents and solvent combinations as to their capacity of dissolving Tamoxifen Citrate. The solutions are made by first mixing the solvent (components) and then adding Tamoxifen Citrate. Each time the maximum quantity of Tamoxifen Citrate is determined at which the solution is still stable. The results are outlined in the following table. The percentages given are all % by weight.

TABLE

| Solvent components | Solubility (mg/ml) | Suitable? |
|---|---|---|
| water | 0.165 | no |
| 5% of ethanol in water | 0.283 | no |
| 10% of ethanol in water | 0.424 | no |
| 15% of ethanol in water | 0.666 | no |
| 5% of propylene glycol and 5% of ethanol in water | 0.324 | no |
| 5% of propylene glycol and 10% of ethanol in water | 0.761 | no |
| 5% of propylene glycol and 15% of ethanol in water | 0.831 | no |
| 10% of propylene glycol, 10% of ethanol, and 0.3% of polysorbate 80 in water | 1.47 | just |
| 10% of ethanol, 50% of glycerol and 20% of sorbitol solution in water | 3.007 | yes |
| 10% of ethanol, 10% of propylene glycol, 50% of glycerol, and 20% of sorbitol solution in water | 3.5 | well |
| 15% of ethanol, 10% of propylene glycol, 50% of glycerol, 20% of sorbitol solution in water | 6.0 | excellently |

I claim:

1. A pharmaceutical preparation which provides a dosage form of Tamoxifen, wherein the dosage form comprises at least 1.5 mg/ml of Tamoxifen Citrate, in the absence of a complexing agent, in a pharmaceutically acceptable solution which is administered orally.

2. A pharmaceutical preparation according to claim 1, wherein the solution comprises a solvent comprising the following components: (a) from about 10% to 20% by weight of ethanol; (b) from about 10% to 60% by weight of glycol; and (c) water in a volume percentage adding up to 100% by volume.

3. A pharmaceutical preparation according to claim 2, wherein the glycol component is a mixture of propylene glycol and glycerol.

4. A pharmaceutical preparation according to claim 3, wherein the water component (c) contains a bulk-sweetening agent.

5. A pharmaceutical preparation according to claim 4, wherein the bulk-sweetening agent is from 15% to 25% by weight of sorbitol.

6. A pharmaceutical preparation according to claim 5, wherein the solvent comprises the following components: 15% by weight of ethanol, 10% by weight of propylene glycol, 50% by weight of glycerol, 20% by weight of a solution of 70% by weight of sorbitol in water, and water in a volume percentage adding up to 100% by volume.

7. A process for the preparation of the solution according to claim 2, comprising dissolving the Tamoxifen Citrate in a mixture of the ethanol and glycol components, and then adding the water component and any other additives.

8. A process for the preparation of a solution according to claim 2, comprising the steps of first dispersing Tamoxifen Citrate in the glycol component and then adding the ethanol component and the water component.

9. A process for the preparation of a solution in accordance with claim 3, comprising dispersing Tamoxifen Citrate in the propylene glycol to form a dispersion, adding the dispersion to the glycerol, then adding the ethanol component thereto to form a solution, and then adding the water component.

10. A pharmaceutical preparation according to claim 2, wherein the water component (c) contains additive(s) selected from the group consisting of flavors, sweeteners, and coloring agents.

11. A process according to claim 9, wherein the water component contains additive(s) selected from the group consisting of flavors, sweeteners and coloring agents.

* * * * *